(12) United States Patent
Yamagata

(10) Patent No.: US 6,822,447 B1
(45) Date of Patent: Nov. 23, 2004

(54) SPHERICAL MAGNETIC RESONANCE IMAGING APPARATUS

(75) Inventor: Hitoshi Yamagata, Tochigi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/391,399

(22) Filed: Sep. 8, 1999

(30) Foreign Application Priority Data

Sep. 30, 1998 (JP) .......................................... 10-279172

(51) Int. Cl.$^7$ ................................................ G01V 3/00
(52) U.S. Cl. ...................... 324/318; 324/320; 324/309
(58) Field of Search ................................. 324/318, 320, 324/322, 307, 309, 319; 600/410, 411, 422, 415; 335/299, 216

(56) References Cited

U.S. PATENT DOCUMENTS

| | | | | |
|---|---|---|---|---|
| 4,595,899 A | * | 6/1986 | Smith et al. ................. | 335/216 |
| 4,689,591 A | * | 8/1987 | McDougall ................. | 335/299 |
| 4,829,252 A | | 5/1989 | Kaufman .................... | 324/309 |
| 4,968,937 A | * | 11/1990 | Akgun ....................... | 324/318 |
| 5,197,474 A | * | 3/1993 | Englund et al. ............ | 600/415 |
| 5,291,169 A | | 3/1994 | Ige et al. .................... | 335/216 |
| 5,735,278 A | * | 4/1998 | Hoult et al. ................ | 600/422 |
| 5,814,993 A | * | 9/1998 | Frese et al. ................. | 324/319 |
| 5,899,857 A | * | 5/1999 | Wilk .......................... | 600/407 |
| 5,924,987 A | * | 7/1999 | Meaney et al. ............. | 600/420 |
| 6,049,208 A | * | 4/2000 | Takekoshi et al. .......... | 324/319 |
| 6,094,590 A | * | 7/2000 | Kan et al. ................... | 600/411 |
| 6,112,110 A | * | 8/2000 | Wilk .......................... | 600/407 |
| 6,128,522 A | * | 10/2000 | Acker et al. ................ | 600/411 |
| 6,198,957 B1 | * | 3/2001 | Green ......................... | 600/411 |
| 6,317,619 B1 | * | 11/2001 | Boernert et al. ............ | 600/410 |

FOREIGN PATENT DOCUMENTS

JP H2-191437 7/1990

* cited by examiner

*Primary Examiner*—Diego Gutierrez
*Assistant Examiner*—Tiffany A. Fetzner
(74) *Attorney, Agent, or Firm*—Nixon & Vanderhye PC

(57) ABSTRACT

In a magnetic resonance imaging apparatus, a transmitting/receiving coil is attached to a patient at a region of interest and disposed within a static magnetic field, a radio-frequency magnetic field, and a gradient magnetic field and an image of the patient is obtained. A tabletop is used to move the patient in the static field in a horizontal direction within a horizontal plane and up and down in a direction that is perpendicular to the horizontal plane, a patient couch controller causing the tabletop to move, based on the position of the region of interest obtained from the image so that the position of the region of interest is caused to coincide in three dimensions with center of the static magnetic filed and/or the gradient magnetic field.

12 Claims, 12 Drawing Sheets

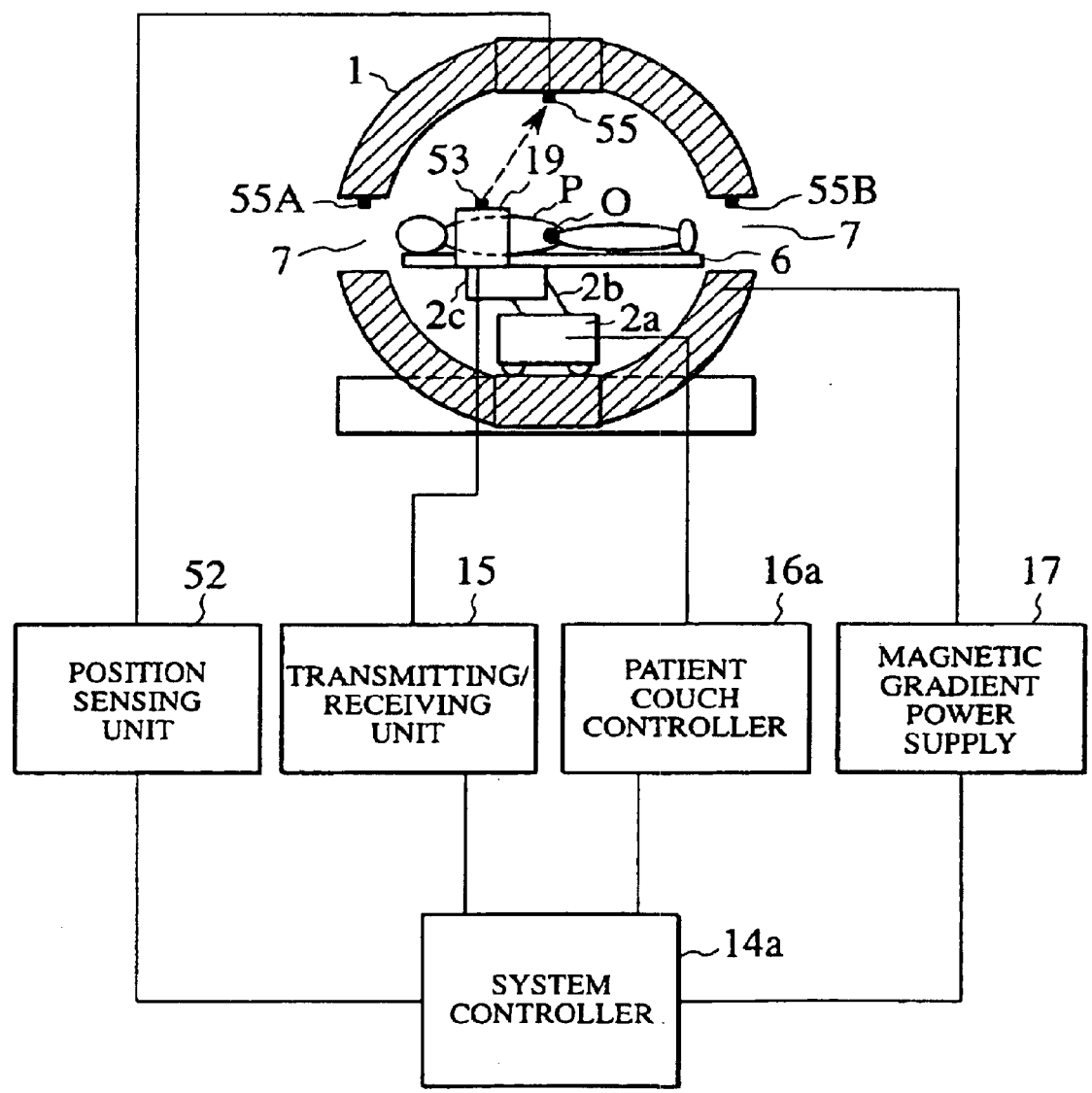

SPHERICAL MAGNETIC RESONANCE IMAGING APPARATUS

BACKGROUND OF THE INVENTION

1. Field of the Invention

The present invention relates to a magnetic resonance imaging apparatus, especially useful for an open-type MRI apparatus that has an open magnet gantry.

2. Description of the Related Art

Earlier open-type MRI systems include a vertical field type MRI system (MRI system with open access to patient image volume), featuring open access to the patient image volume, as disclosed for example in U.S. Pat. No. 4,829,252.

In an MRI system featuring good open access, such as the above-noted vertical field type of open MRI system or a tubular type MRI system of the past with a short axis and large diameter, the patient couch is moved front and back and to the left and right at a uniform height with respect to the patient transport axis when acquiring images. In this case, in the open MRI system, there are not good gradient magnetic field linearity and static magnetic field uniformity in comparison with the earlier tubular type MRI system. However, because there is good magnetic field uniformity at the center of the gradient magnetic field and static magnetic field, if images of the region of treatment of the patient are acquired at the center position of the magnetic field, high-quality images of the region of treatment are obtained. In this case, there is needed a complicated process in which a mark from a positioning projector is set on a specific point of the patient or T/R coil before moving the patient into the gantry as a preparation of setting the patient on the center of the magnetic field. This is to inform the MRI main unit of distance information between the mark and the center of the magnetic field in a front/rear direction and a right/left direction with respect to the patient transport axis.

When operating the above-noted type of open MRI as an interventional apparatus, for example, the region (location) of treatment is often not large, but limited to a specific area. In the case, even if the patient couch is moved within a horizontal plane with respect to the patient transport axis at a uniform height, it was either extremely difficult or impossible to position the region of treatment at the center of the gradient magnetic field and static magnetic field in three dimensions.

For this reason, the images obtained from such MRI systems in the past exhibited a great deal of image distortion, image non-uniformities, and fat artifacts, making it difficult to use the images in treatment.

SUMMARY OF THE INVENTION

Accordingly, it is an object of the present invention to provide a magnetic resonance imaging apparatus which enables quick positioning of the region of treatment or diagnosis at the center of the gradient magnetic field and static magnetic field, and enables the acquisition of highly precise, high-quality images, with reduced image distortion, non-uniformities, and fat artifacts.

In order to achieve the above-noted object, a magnetic resonance imaging apparatus according to the present invention comprises:

a static magnetic field generator for generating a static field;

a gradient magnetic field generator for generating a gradient magnetic field that is superimposed on the static magnetic field;

a radio-frequency magnetic field pulse transmitting/receiving unit, which applies a radio-frequency pulse to a region of interest of the patient that is located within the static magnetic field, and which also receives a magnetic resonance signal that is generated from the patient;

a patient couch, which enables movement of the patient;

a position information establishing apparatus which establishes position information of the region of interest of the patient; and a patient couch controller for moving the patient couch, based on the region of interest position information, so that the region of interest is positioned either at the center of the static magnetic field, or at the center of the gradient magnetic field.

According to the present invention, because a patient couch controlling means causes the movement of the movable patient couch, so as to position the region of interest of the patient at the center of either the static magnetic field or the gradient magnetic field, it is possible to obtain precise, high-quality images, with reduced image distortion, non-uniformities, and fat artifacts.

Another aspect of the present invention is a method for performing magnetic resonance imaging diagnosis, this method comprising the steps of:

placing the patient onto a patient couch that is disposed within a static magnetic field and a gradient magnetic field;

moving the patient couch approximately, based on a signal from a position detector, so that the region of interest of the patient approximately coincides with the center of the static magnetic field or the center of the gradient magnetic field;

applying a radio-frequency pulse to the region of interest of the patient, and receiving a magnetic resonance signal that is generated from the patient;

reproducing a plurality of images of the patient, based on the magnetic resonance signal;

selecting an image that includes the region of interest from the plurality of images of the patient; and moving the patient couch, based on the selected image, so that the region of interest of the patient coincides precisely with the center of the static magnetic field or the center of the gradient magnetic field.

The above-noted method of diagnosis according to the present invention provides the same effect as the earlier described magnetic resonance imaging apparatus.

BRIEF DESCRIPTION OF THE DRAWINGS

FIG. 13 is a system block diagram that shows an MRI apparatus according to the second embodiment of the present invention.

DETAILED DESCRIPTION OF THE PREFERRED EMBODIMENTS

Preferred embodiments of the present invention are described in detail below, with reference to relevant accompanying drawings.

First Embodiment

Figure 1:
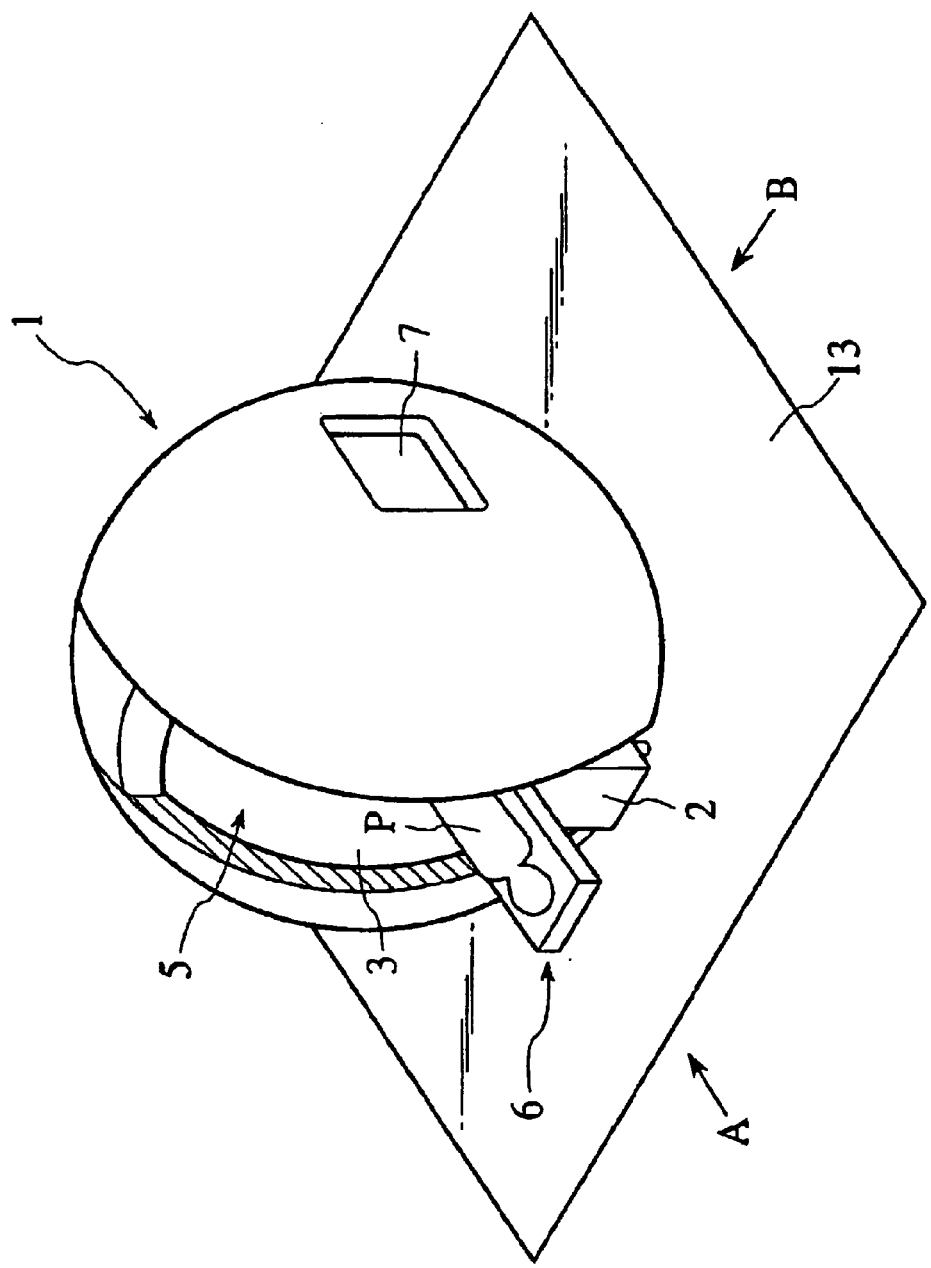
FIG. 1 is a perspective view that shows an outer view of an open-type MRI apparatus according to the first embodiment of the present invention.

FIG. 1 shows perspective outer view of an open-type MRI apparatus according to the first embodiment of the invention. In this drawing, the arrow A indicates the front direction as seen from the front of the MRI apparatus, the arrow B indicates the side direction, and the arrow C indicates the top direction. Though a similar MRI apparatus is described in Japanese Patent Application No. 9-112452, the present invention is not limited by this shape of this MRI apparatus.

The main enclosure 1 (hereinafter generally referred to as the magnet gantry1), has within it such elements as a static field magnet, a magnetic gradient coil, and an excitation (RF) coil for use with respect to the entire body of the patient. A patient couch 2 can move freely over the floor surface 13, and a tabletop 6, on which a patient P is placed, is mounted to the top part of the patient couch 2.

The magnet gantry 1 is of spherical shape and, seen from the direction of arrow A, has a space 3 formed in it, this space having a width such that it is possible to insert the patient couch 2 into the center part of the magnet gantry 1. The center of the magnet gantry 1 has a spherically shaped inner space 5, which houses the patient couch 2, including the tabletop 6, and is of sufficient size as to allow the rotation of the patient couch 2 in an arbitrary direction (for example, in the horizontal direction).

The patient couch 2 is provided with a rotational drive mechanism (not shown in the drawing) for the purpose of rotationally driving the tabletop 6, onto which the patient is placed, at least 90 degrees within the horizontal plane after the patient couch 2 is placed in the center of the inner space 5.

An access port 7 through which the inner space 5 communicates with the outside of the magnet gantry 1 is provided in the side part of the magnet gantry 1 as seen from the direction of arrow B. A similar access port is also provided on the opposite side of the inner space 5.

The access port 7 allows passage of part of the tabletop 6 when the patient couch 2 is housed within the inner space 5, and is of sufficient width to allow the patient P that is disposed horizontally to pass through the center part on both sides, so as to position the region of diagnosis or region of treatment at the center of the magnet.

According to the above-noted configuration, it is possible for a physician, for example, to enter the inner space 5 via the space 3 formed in the magnet gantry 1, and possible for a physician, for example, to approach the patient couch 2 onto which the patient P is placed, from the side.

Figure 2:
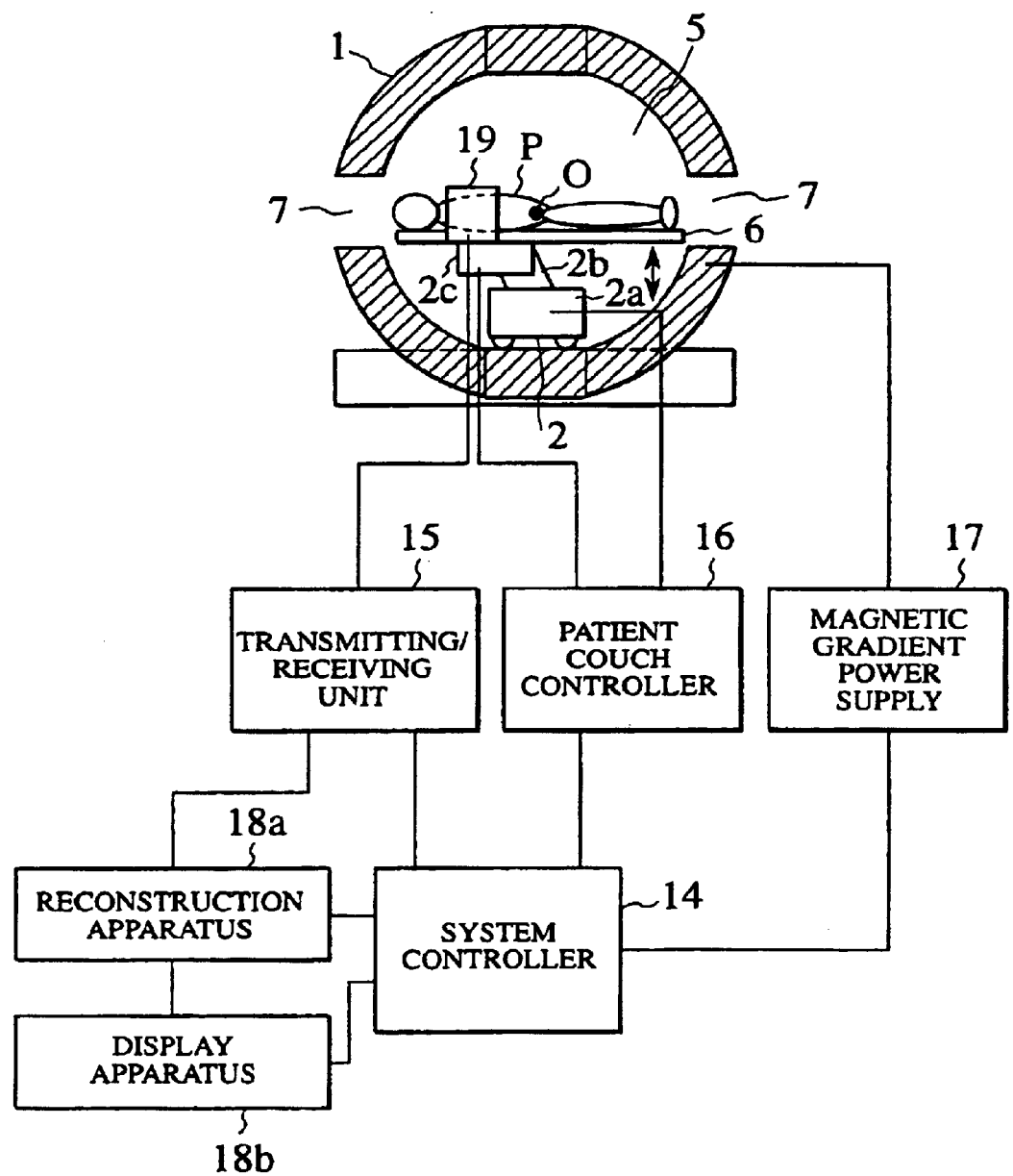
FIG. 2 is a system block diagram of the MRI apparatus according to the second embodiment of the present invention.
Figure 3:
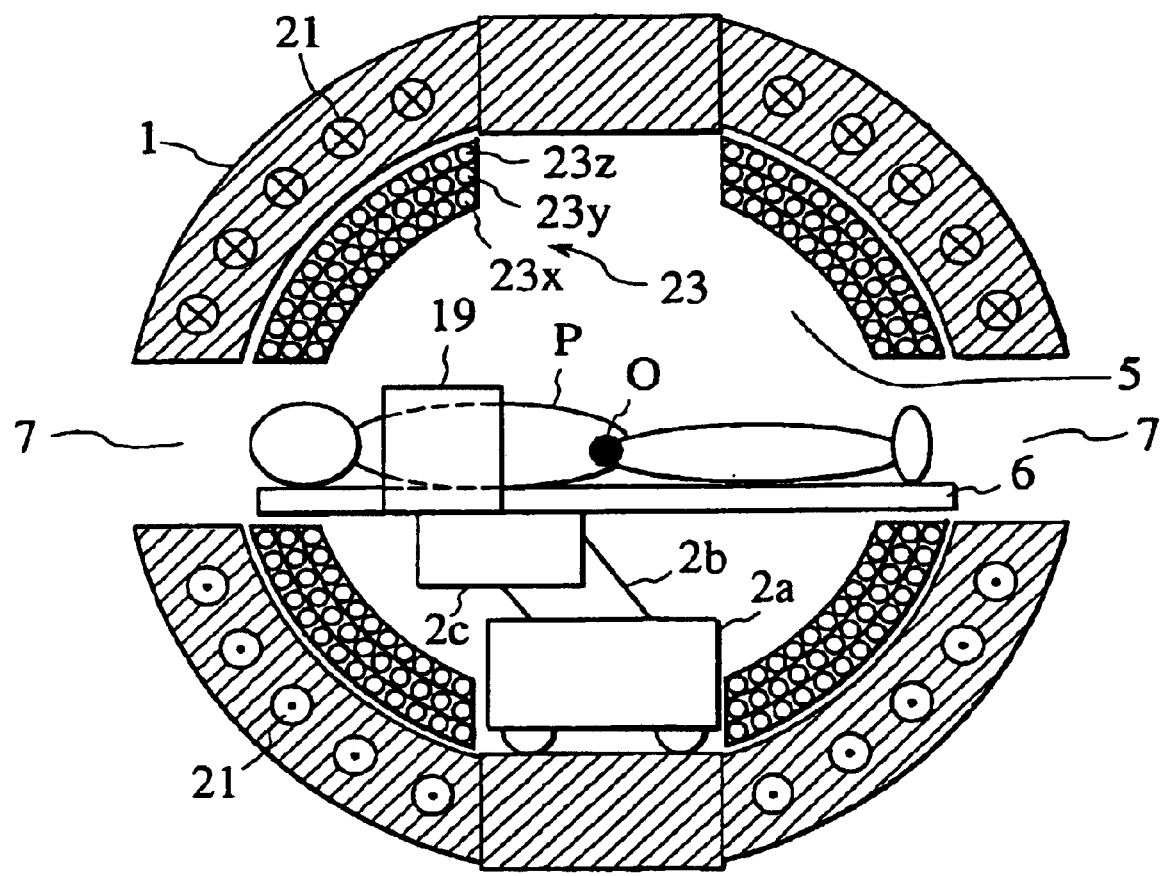
FIG. 3 is a drawing that shows the arrangement of the static field magnet and the magnetic gradient coil.

FIG. 2 shows a system block diagram of the MRI apparatus according to the first embodiment of the present invention, and FIG. 3 shows the arrangement of the static field magnet and the magnetic gradient coil. In FIG. 2, the cross-section of the magnet gantry 1 as seen from the frontal direction thereof is shown. In this case, by placing the patient couch 2, inserted via the space 3, into the inner space 5 of the magnet gantry 1, and rotating the tabletop 6 by means of the rotational drive mechanism of the patient couch 2, the body axis of the patient P is aligned in the direction of the access port 7.

In the above condition (with the patient P in a condition that enables image acquisition), or before and after this condition, a transmitting/receiving (T/R) coil 19 is attached at, for example, the chest area of the patient P. The T/R coil 19 can be replaced by a receiver coil according to the purpose of the diagnosis.

The patient couch 2 can move the tabletop 6 forward and back, to the left and right (horizontal directions) and up and down (vertical directions), and is formed by a patient couch base 2a, a horizontal movement screw box 2c, which has a horizontal movement mechanism for the purpose of moving the tabletop 6 in a horizontal direction, and a linking section 2b, which links the base 2a and the horizontal movement screw box 2c of the patient couch 2 and which has a vertical movement mechanism for the purpose of moving the tabletop 6 up and down. In FIG. 2, the center O indicates the center of the static magnetic field and the center of the gradient magnetic field the horizontal movement mechanism and vertical movement mechanism will be described below.

A static field magnet 21, as shown in FIG. 3, is disposed along the substantially spherical inner space 5, and is formed by a coil bundle made of either a superconductor or a conventional conductor, through which a circulating current passes, resulting in a magnetic field that is uniform with respect to the body axis of the patient (Z axis) being applied to the patient P.

A magnetic gradient coil 23 is formed by an X-axis magnetic gradient coil 23x, a Y-axis magnetic gradient coil 23y, and a Z-axis magnetic gradient coil 23z, these coils being driven by a magnetic gradient power supply 17. These magnetic gradient coils apply gradient magnetic fields Gx, Gy, and Gz, the magnetic field intensity of which vary linearly, in the X and Y directions within a desired cross-section of the patient P, and in the Z direction, which is perpendicular with respect to the X and Y directions.

With this arrangement because the static field magnet 21 is provided along the inner space 5, the coil pattern of the static field magnet 21 is spherical, enabling enhancement of the uniformity of the static magnetic field developed by the static field magnet.

The above-noted MRI apparatus also has a system controller 14, a transmitting/receiving (T/R) unit 15, a patient couch controller 16, a magnetic gradient power supply 17, a reconstruction apparatus 18a and a display apparatus 18b. The T/R unit 15, under control from the system controller 14, generates a radio-frequency magnetic field with respect to the patient P by applying a radio-frequency signal to the T/R coil 19, receiving from the T/R coil 19 a magnetic resonance signal generated from the patient P with the application of a static magnetic field, a gradient magnetic field and a radio-frequency magnetic field, amplifying and detecting the received signal, and then A/D converting and sending the signal to the reconstruction apparatus 18a.

The reconstruction apparatus 18a performs image configuration processing, including Fourier transformation, with respect to data input to it from the T/R unit 15. The display apparatus 18b displays a cross-sectional image of the patient P that was reconstructed by the reconstruction apparatus 18a.

The patient couch controller 16, under the control of the system controller 14, outputs movement information for the purpose of moving the tabletop 6 to the patient couch 2, this information indicating the amount of horizontal movement of the tabletop 6 and the amount of up and down movement of the tabletop 6.

The patient couch controller 16 outputs movement amount information to the patient couch 2 for the purpose of moving the patient couch 2 so that the center of the region of imaging (region of diagnosis or region of treatment) of the patient P is caused to coincide with the center of the static magnetic field and center of the gradient magnetic field. The patient couch 2, in response to the movement amount information from the patient couch controller 16, moves the tabletop 6 in the horizontal and vertical directions, using the horizontal movement mechanism and vertical movement mechanism.

(Horizontal Movement Mechanism)

Figure 4A:
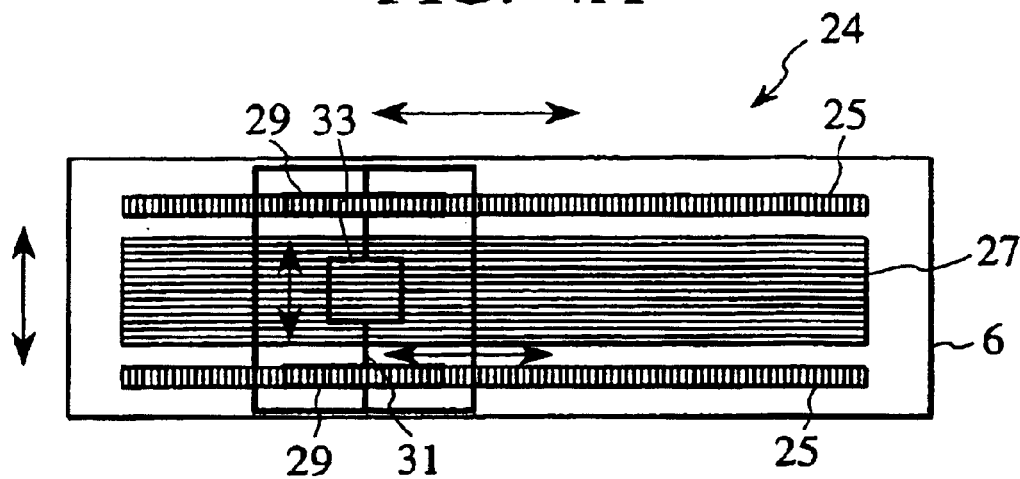
FIG. 4A and FIG. 4B are drawings which show the horizontal movement mechanism of the patient couch which is provided in the MRI apparatus according to the first embodiment of the present invention.
Figure 4B:
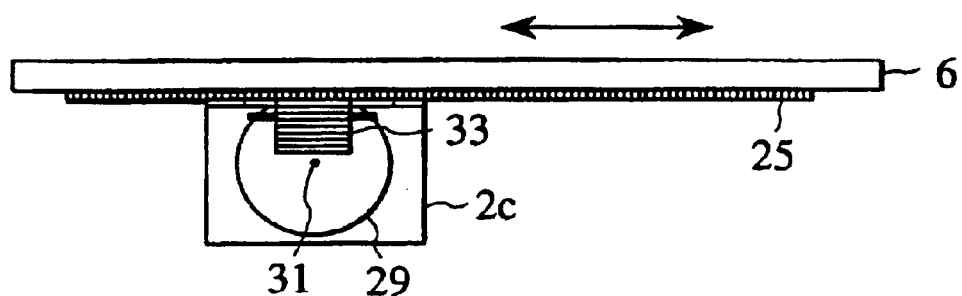

FIG. 4A and FIG. 4B show the horizontal movement mechanism of the patient couch that is provided in the MRI apparatus according to the first embodiment of the present invention. FIG. 4A provides a rear view of the horizontal movement screw box and the horizontal movement mechanism that is provided on the tabletop. FIG. 4B provides a side view of the horizontal movement screw box and the horizontal movement mechanism that is provided on the tabletop. The horizontal movement mechanism 24 is described below, with reference made to FIG. 4A and FIG. 4B.

Referring to FIG. 4A, on the rear side of the tabletop 6 are formed two rows of front-to-back movement screw grooves 25, on the left and right, for the purpose of moving the tabletop 6 forward and back, and left-to-right movement screw grooves 27, disposed between the two rows of front-to-back movement screw grooves 25, for the purpose of moving the tabletop 6 to the left and right.

Inside the horizontal movement screw box 2c are provided front-to-back movement screws 29, which is disposed so as to mesh with the front-to-back movement screw grooves 25, and a left-to-right movement screw 33, which is disposed so as to mesh with the left-to-right movement screw grooves 27. The front-to-back movement screw 29 and the left-to-right movement screw 33 are mounted to a shaft 31.

According to a horizontal movement mechanism configured as noted above, when movement amount information that indicates an amount of horizontal movement is sent from the patient couch controller 16, the screws 29 and 33 rotate in response to this amount of horizontal movement information sent from the patient couch controller 16. For this reason, the screw grooves 25 and 27 that mesh with the screws 29 and 33 move, thereby causing the tabletop 6 to move within the horizontal plan (front-to-back and left-to-right), in response to the amount of horizontal movement that was received.

(Vertical Movement Mechanism)

Figure 5:
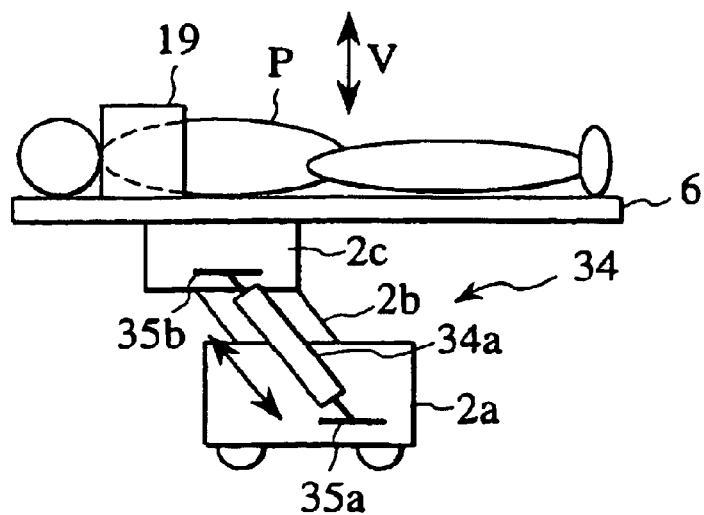
FIG. 5 is a drawing that shows the vertical movement mechanism of the patient couch which is provided in the MRI apparatus according to the first embodiment of the present invention.

Turning to FIG. 5, we see the vertical movement mechanism that is provided in the MRI apparatus according to the first embodiment of the present invention. As shown in FIG. 5, a vertical movement mechanism 34, which causes the tabletop 6 to move up and down, is provided on the tabletop 6.

The vertical movement mechanism 34 is formed by a first holding section 35a, which is mounted to one end of a hydraulic cylinder 34a and which is provided in the patient couch base 2a, and a second holding section 35b, which is mounted to the other end of the hydraulic cylinder 34a and which is provided in the horizontal movement screw box 2c. The hydraulic cylinder 34a causes the horizontal movement screw box 2c to move up and down, with respect to the position of the patient couch base 2a, in response to hydraulic pressure.

According to a vertical movement mechanism 34 configured as noted above, when amount of movement information indicating the amount of vertical movement is sent from the patient couch controller 16, the hydraulic cylinder 34a, in response the amount of vertical movement information from the patient couch controller 16, uses hydraulic pressure to cause the horizontal movement screw box 2c to move up and down, via the second holding section 35, thereby enabling the up and down movement of the tabletop 6.

Figure 6A:
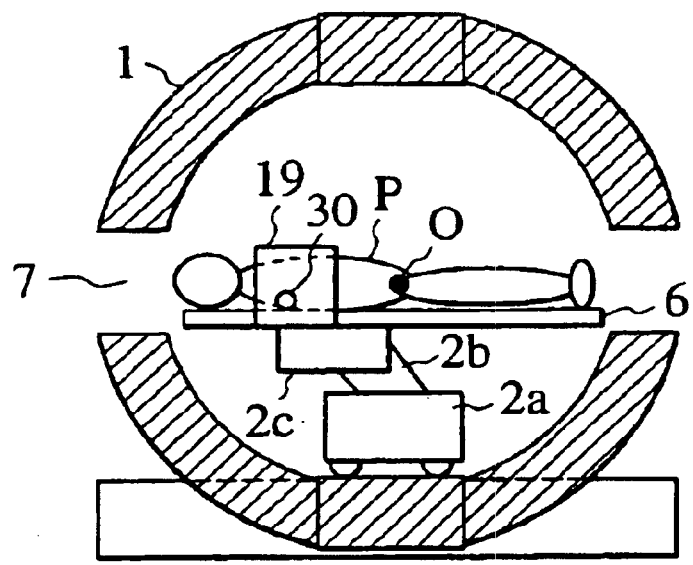
FIG. 6A and FIG. 6B are drawings that illustrates the positioning of the region of interest of the patient at the center of the static magnetic field and the center of the gradient magnetic field.
Figure 6B:
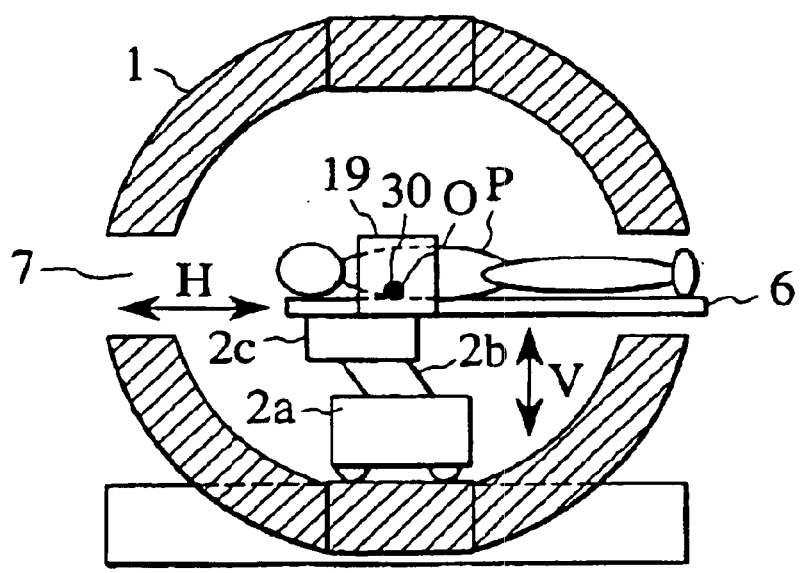

An MRI apparatus having the horizontal movement mechanism 24 and the vertical movement mechanism 34 configured as described above will now be described. FIG. 6A and FIG. 6B illustrate the positioning of the region of treatment of a patient placed in an MRI apparatus according to the first embodiment, so as to cause this region to coincide with the center of the static magnetic field and the gradient magnetic field. FIG. 6A show the condition of the patient before performing positioning of the position of diagnosis with the center of the magnetic field, and FIG. 6B shows the condition of the patient after positioning the region of diagnosis with the center of the magnetic field.

When performing positioning of the region of diagnosis (or treatment) with the center of a magnetic field (static or gradient magnetic field) the T/R coil 19 is first attached at the region of diagnosis, such as the chest part of the patient, as shown in FIG. 6A. Then, a manual or mechanical means is used to approximately align the tabletop 6 to the region of diagnosis 30 of the patient P, so that the region of diagnosis 30 is positioned in the area of the center O of the static magnetic field and gradient magnetic field by approximately positioning the tabletop 6.

Figure 7:
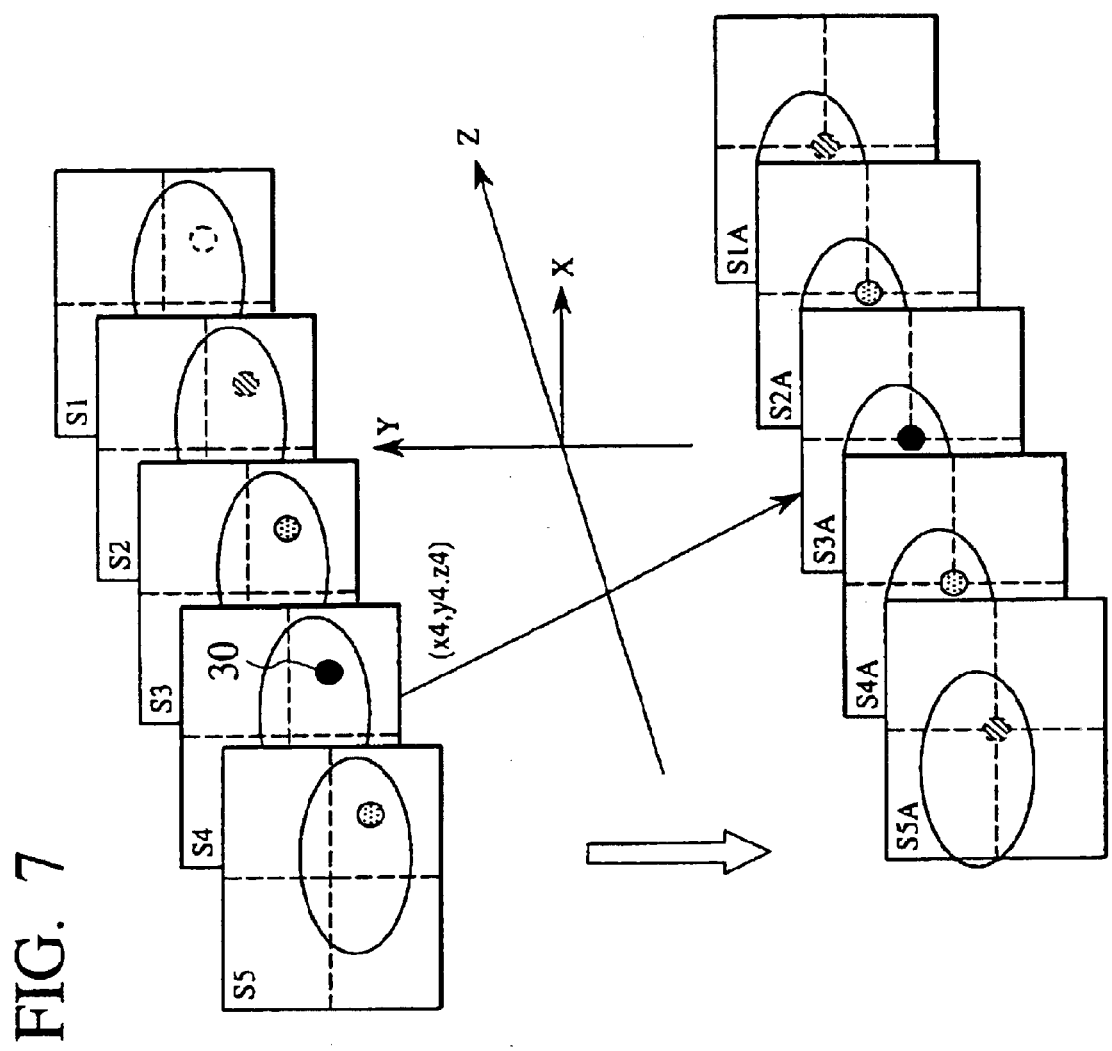
FIG. 7 is a drawing that shows a positioning scan.

Next, after approximate positioning of the tabletop 6, to facilitate positioning of the region of diagnosis 30, the T/R unit 15, reconstruction apparatus 18a, and display apparatus 18b shown in FIG. 2 are used to perform a high-speed positioning scan of a 2-dimensional T1W multislice image, for example, in the horizontal direction near the region of diagnosis 30 of the patient P, as shown in FIG. 7, thereby obtaining the multislice images S1 through S5 along the Z-axis (body axis of the patient P).

Then, using a pointing device such as a mouse (not shown in the drawing), a slice such as S4, which is the closest to the region of diagnosis 30, is selected. Essentially, after performing approximate positioning of the region of diagnosis 30 within the horizontal plane, a multislice image is used to perform Z-axis positioning of the region of diagnosis 30. The pointing device is further used to select the region of diagnosis 30 on the selected image to perform further positioning for X- and Y- axes.

Additionally, the system controller 14 outputs the position information of the coordinates (x4, y4, and z4) of the region of diagnosis 30 in the selected slice image S4. Then, the difference (distance) components between the position information (corresponding to the region of diagnosis 30 position) of the image S4 that is sent from the patient couch controller 14 and the position information for the center O of the static magnetic field and the gradient magnetic field are calculated, and then controls the patient couch 2 so as to move the tabletop 6 by the calculated distance difference components.

When this is done, the horizontal movement mechanism 24 and the vertical movement mechanism 34 move the tabletop 6 in the horizontal and vertical directions, respectively, by the difference components, so that the region of diagnosis 30 is quickly moved so as to coincide with the center O of the static magnetic field and the gradient magnetic field, as shown in FIG. 6B.

Essentially, because the uniformity of the static magnetic field and the linearity of the gradient magnetic field are better the closer the position is to the center O of these fields, by moving the patient couch in three dimensions, including vertical movement to that region so as to establish the position of the region of diagnosis 30 at this center O, it is possible to obtain highly precise, high-quality images, with reduced image distortion, non-uniformities, and fat artifacts.

Additionally, by moving the patient couch up and down immediately before and after diagnosis and treatment, it is possible for a physician or a technician to prepare or provide care to the patient P at an appropriate height.

The setting of the position of the region of diagnosis 30 can be done, for example, by the operator pointing to the position 30 from a multislice image from the slice image S1 through the slice image S5, and can also be performed automatically by means of image processing.

Figure 8:
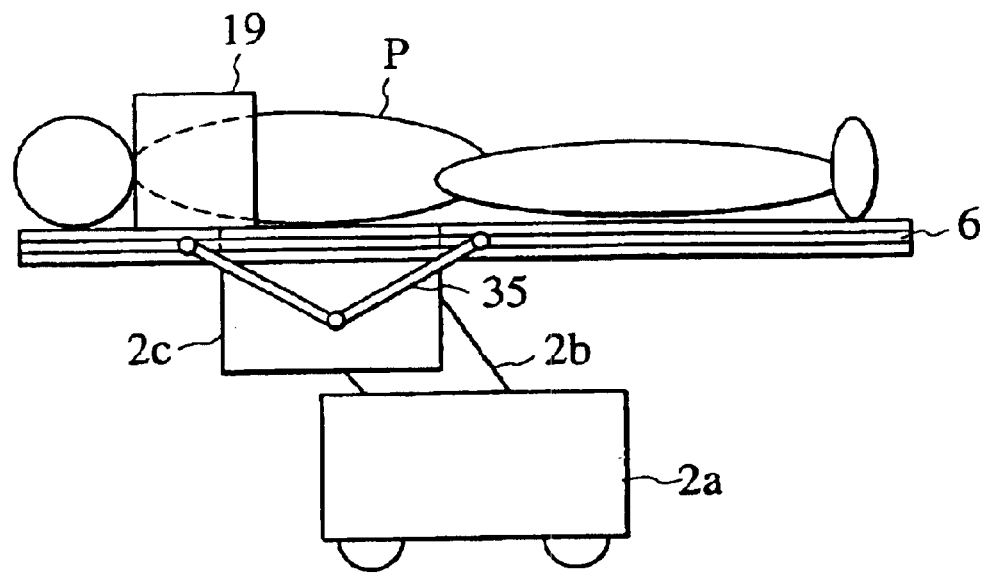
FIG. 8 is a drawing that shows another embodiment of a patient couch, which includes a tabletop holding mechanism.
Figure 9:
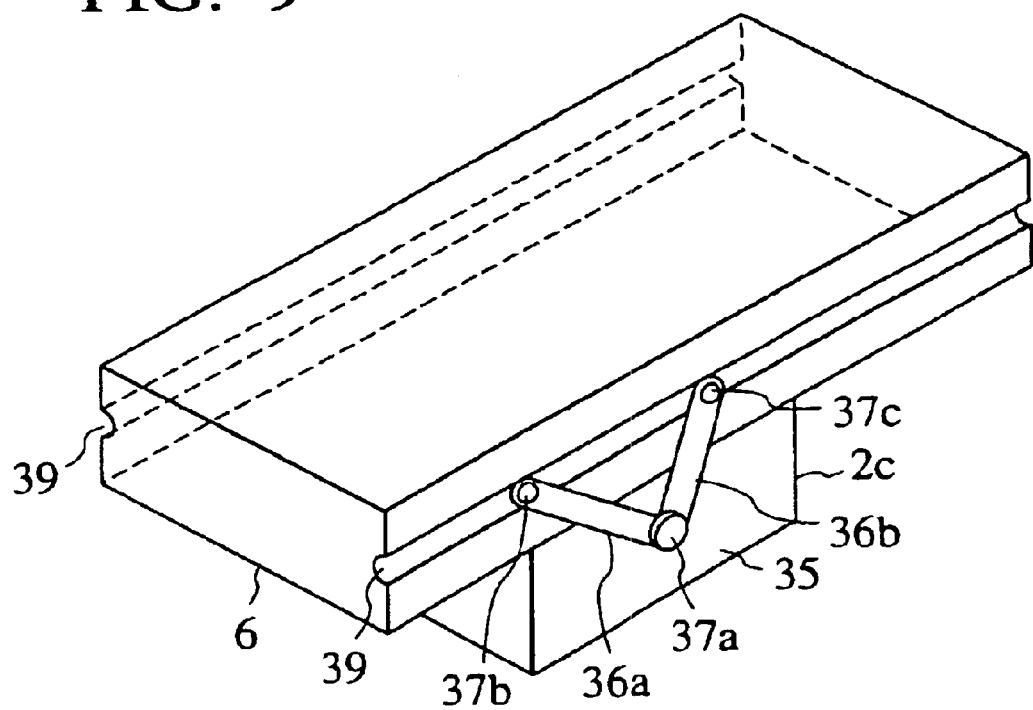
FIG. 9 is a perspective view of the tabletop of FIG. 8.
Figure 10:
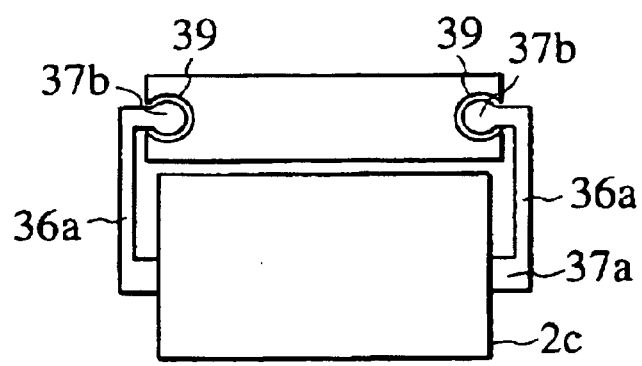
FIG. 10 is a cross-section view of the tabletop of FIG. 8.

Another embodiment of the patient couch, which includes a tabletop horizontal holding mechanism, is shown in FIG. 8. FIG. 9 is a perspective view of the tabletop horizontal holding mechanism of FIG. 8. FIG. 10 is a cross-section view of the tabletop horizontal holding mechanism of FIG. 8. The tabletop horizontal holding mechanism 35, as shown in FIG. 8, holds the tabletop 6 horizontally when the tabletop 6 is moved forward and back with respect to the patient couch 2.

This tabletop horizontal holding mechanism 35 has a configuration such as shown in FIG. 9. The horizontal movement screw box 2c has the first holding pin 37a mounted to it, one end of the first supporting rod 36a and the second supporting rod 36b being mounted to this first holding pin 37a. The other end of the first supporting rod 36a has the second holding pin 37b mounted to it, and the other end of the second supporting rod 36b has the third holding pin 37c mounted to it.

Side grooves 39 are formed on in the front-to-back direction on the tabletop 6, the second holding pin 37b and the third holding pin 37c fitting into these tabletop side grooves 39, so that when the tabletop 6 move forward and back, the tabletop side grooves 39 move so that the second holding pin 37b and the third holding pin 37c slide therein.

According to a tabletop horizontal holding mechanism 35 configured as described above, even if the tabletop 6 moves forward and back with respect to the patient couch 2, the effect of the three holding pins, the first supporting rod 35a, and the second supporting rod 36b is to hold the tabletop 6, so that the tabletop 6 does not tip over. Thus, it is possible to perform work smoothly, without having the patient P tip over.

Figure 11:
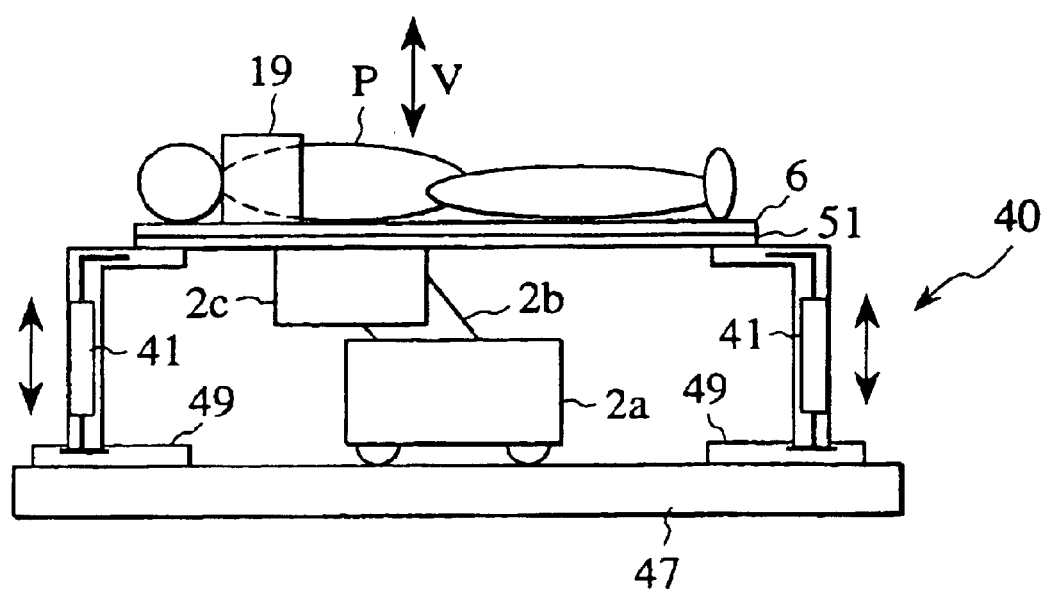
FIG. 11 is a drawing that shows another embodiment of a vertical movement mechanism of the patent transporter.
Figure 12:
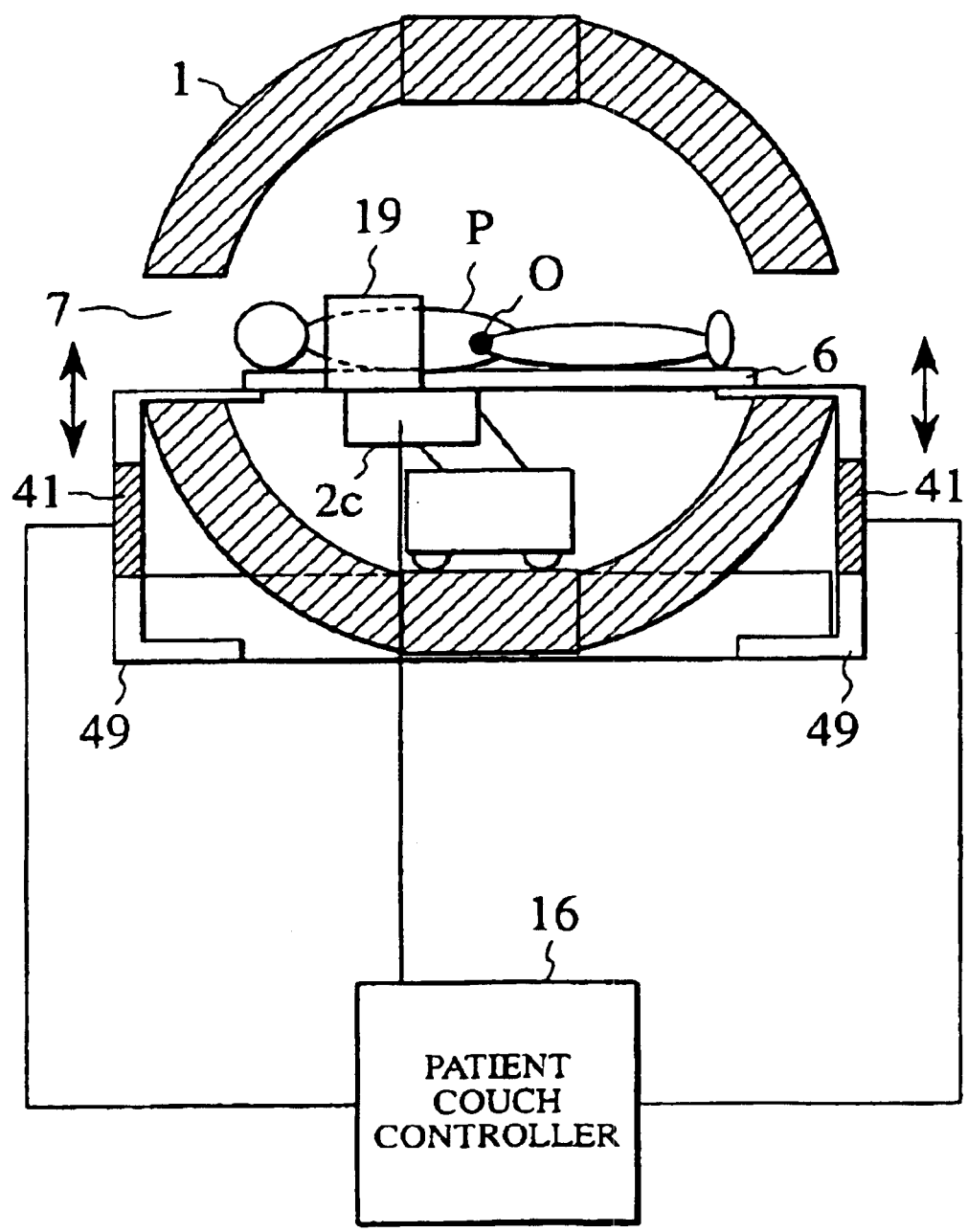
FIG. 12 is a drawing that shows the patient couch control system, which includes another embodiment of a vertical movement mechanism of the patent transporter.

Another embodiment of the vertical movement mechanism of the patient couch is shown in FIG. 11. FIG. 12 shows a patient couch control system that includes this embodiment of a vertical movement mechanism for the patient couch.

The vertical movement mechanism 40 of the patient couch shown in FIG. 11 is configured as follows. Vertical movement mechanism main units 49 are provided at the bead end and at the feet end of the floor surface 47 with respect to the patient P, a hydraulic cylinder 41 being disposed within each of these vertical movement mechanism main units 49.

A liner 51, which is mounted to the horizontal movement screw box 2c is disposed at the top ends of the two vertical movement mechanism main units 49, this liner 51 is supported at both of its ends by the vertical movement mechanism 40. The tabletop 6 is disposed at the top of the liner 51. The hydraulic cylinders 41 use oil pressure to move the liner up and down.

The configuration of the horizontal movement mechanism is that of the horizontal movement mechanism provided in the above-described horizontal movement screw box 2c.

According to a vertical movement mechanism 40 configured as described above and shown in FIG. 12, when movement amount information indicating an amount of vertical movement is sent from the patient couch controller 16, the hydraulic cylinders 41 move the liner 51 up and down by means of hydraulic pressure, in response to the amount of vertical movement sent from the patient couch controller 16, thereby enabling up and down movement of the tabletop 6.

Because of the double structure, having the liner 51 and the tabletop 6, which is supported by the liner 51 and which moves with respect to the liner 51, there is no tilting over of the tabletop 6. Thus, the patient P is not tilted over, and work can be performed smoothly.

Second Embodiment

FIG. 13 shows a system block diagram of an MRI apparatus according to the second embodiment of the present invention. In this embodiment, when performing positioning of the region of diagnosis with the center O of the magnetic field (static magnetic field or gradient magnetic field) a manual or motorized mechanical means is used to automatically perform approximate positioning of the tabletop 6.

For this reason, the MRI apparatus of the second embodiment has a system controller 14a, a T/R unit 15, a patient couch controller 16a, a magnetic gradient power supply 17, a position sensing unit 52, a 3-dimensional position sensor transmitter 53, and a 3-dimensional position sensor receiver 55.

As shown in FIG. 13, the T/R coil 19 that is attached to the region of diagnosis of the patient P has the 3-dimensional (or 2-dimensional) position sensor transmitter 53 mounted to it. A 3-dimensional position sensor receiver 55 is mounted, for example, at the center of the linking section 12 (position corresponding to directly above the magnetic field center O).

The 3-dimensional position sensor receiver 55 receives position information that is sent from the 3-dimensional position sensor transmitter 53. The position sensing unit 52 accepts the position information of the 3-dimensional position sensor transmitter 53 that was received at the 3-dimensional position sensor receiver 55, and sends this information to the system controller 14a.

The system controller 14a sends the position information of the 3-dimensional position sensor transmitter to the patient couch controller 16a. The patient couch controller 16a calculates the difference (distance) components between the position information of the 3-dimensional position sensor transmitter 53 that was sent from the system controller 14a and the position information of the center O of the static magnetic field and gradient magnetic field, and controls the patient couch 2 so as to move the tabletop 6 by the amounts indicated by these difference components.

In the above-noted embodiment, instead of the 3-dimensional position sensor transmitter 53, it is possible to provide a passive type ball or active-type of light receiver, and instead of the 3-dimensional position sensor receiver 55 to provide the transmitter of an optical position sensor. The transmitter can also be provided on the top part of the access port 7 at the front and rear of the magnet gantry 1 (refer to reference numerals 55A and 55B).

Figure 14A:
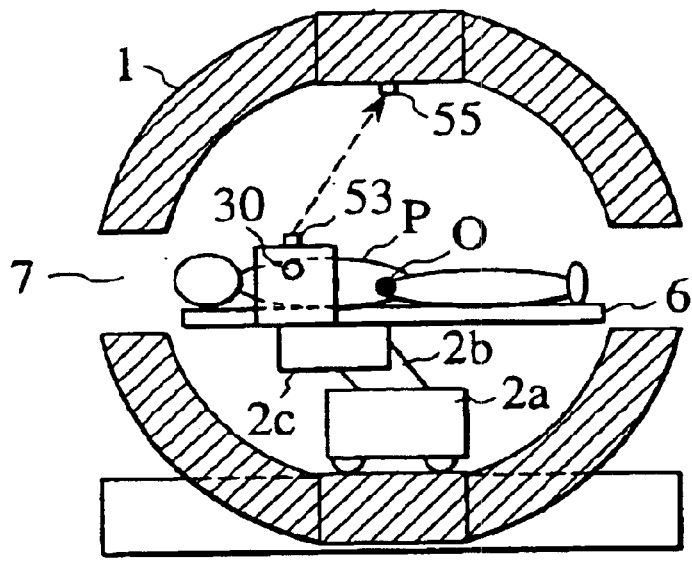
FIG. 14A and FIG. 14B are drawings that show the approximate positioning of the transmitting/receiving coil of the MRI apparatus of the second embodiment of the invention at the center of the static magnetic field and center of the gradient magnetic field.
Figure 14B:
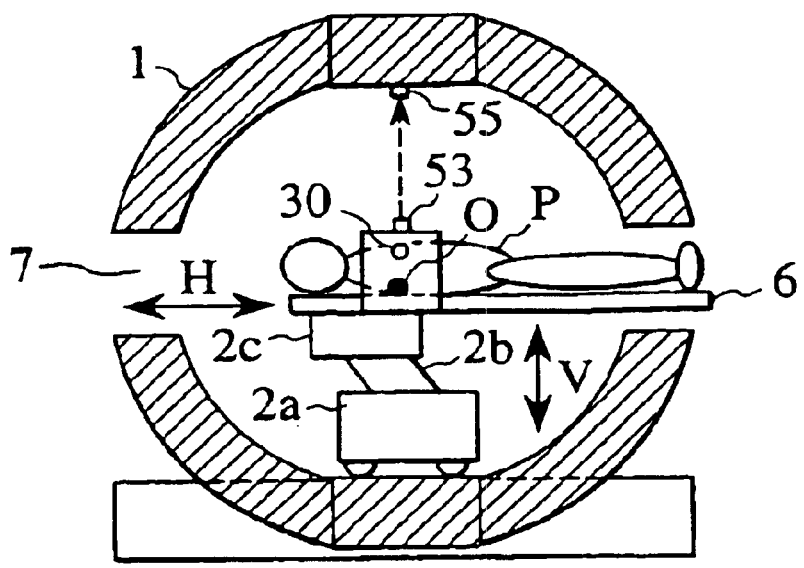

The operation of a MRI apparatus of the second embodiment, configured as described above, is as follows. FIG. 14A and FIG. 14B illustrate the approximate positioning of the T/R coil of an MRI apparatus of the second embodiment at the center of static magnetic field and gradient magnetic field. FIG. 14A shows the condition of the patient P before performing approximate positioning of the T/R coil at the center of the magnetic field, and FIG. 14B shows the condition of the patient P after approximate position of the T/R coil at the center of the magnetic field.

First, as shown in FIG. 14, when position information is sent by the 3-dimensional position sensor transmitter 53, the 3-dimensional position sensor receiver 55 receives this position information, and the position sensing unit 53 detects the position information of the 3-dimensional position transmitter 53 that was received by the 3-dimensional position sensor receiver 55.

Next, the patient couch controller 16a calculates the difference (distance) components from the position information (that is, the center position of the T/R coil 19 that is attached to the region of diagnosis 30) of the 3-dimensional position sensor transmitter 53 sent from the system controller and the position information of the center O of the static magnetic field and the gradient magnetic field and, in order to move the tabletop 6 by just these difference components, moves the tabletop 6 by the amounts of movement (difference components) sent from the patient couch controller 16a, thereby moving the T/R coil 19 to the appropriate position, this being the approximate center O of the magnetic field.

In this manner, because the second embodiment of the MRI apparatus according to the present invention can make an approximate move of the T/R coil 19 to the center of the magnetic field automatically, it is possible to reduce the work load on the operator.

Additionally, after the T/R coil 19 is approximately positioned at the center O of the magnetic field, it is possible as shown in FIG. 7 to perform positioning of the region of diagnosis 30 by means of a positioning scan, so that by merely moving the tabletop 6 by the amount of the difference components between this region of diagnosis 30 position and the magnetic field center O, it is possible to quickly move the region of diagnosis 30 to the center O of the magnetic field.

With the second embodiment of the present invention, it is therefore possible to obtain highly precise, high-quality images, with reduced image distortion, non-uniformities, and far artifacts. Furthermore, by moving the patient couch up and down immediately before and after diagnosis and treatment, it is possible for a physician or a technician to prepare or provide care to the patient P at an appropriate height.

If an image of the position of the T/R coil, which is attached to the patient P, is obtained at a point that is removed from the center O of the magnetic field and different from the above-described position sensor, discrimination is facilitated because of the weakness of the magnetic resonance signal. By using this phenomenon, it is possible to perform approximate movement of the tabletop 6 at the point at which the magnetic resonance signal reaches a given point, while repeatedly moving the imaging and horizontal movement of the tabletop 6.

Figure 15:
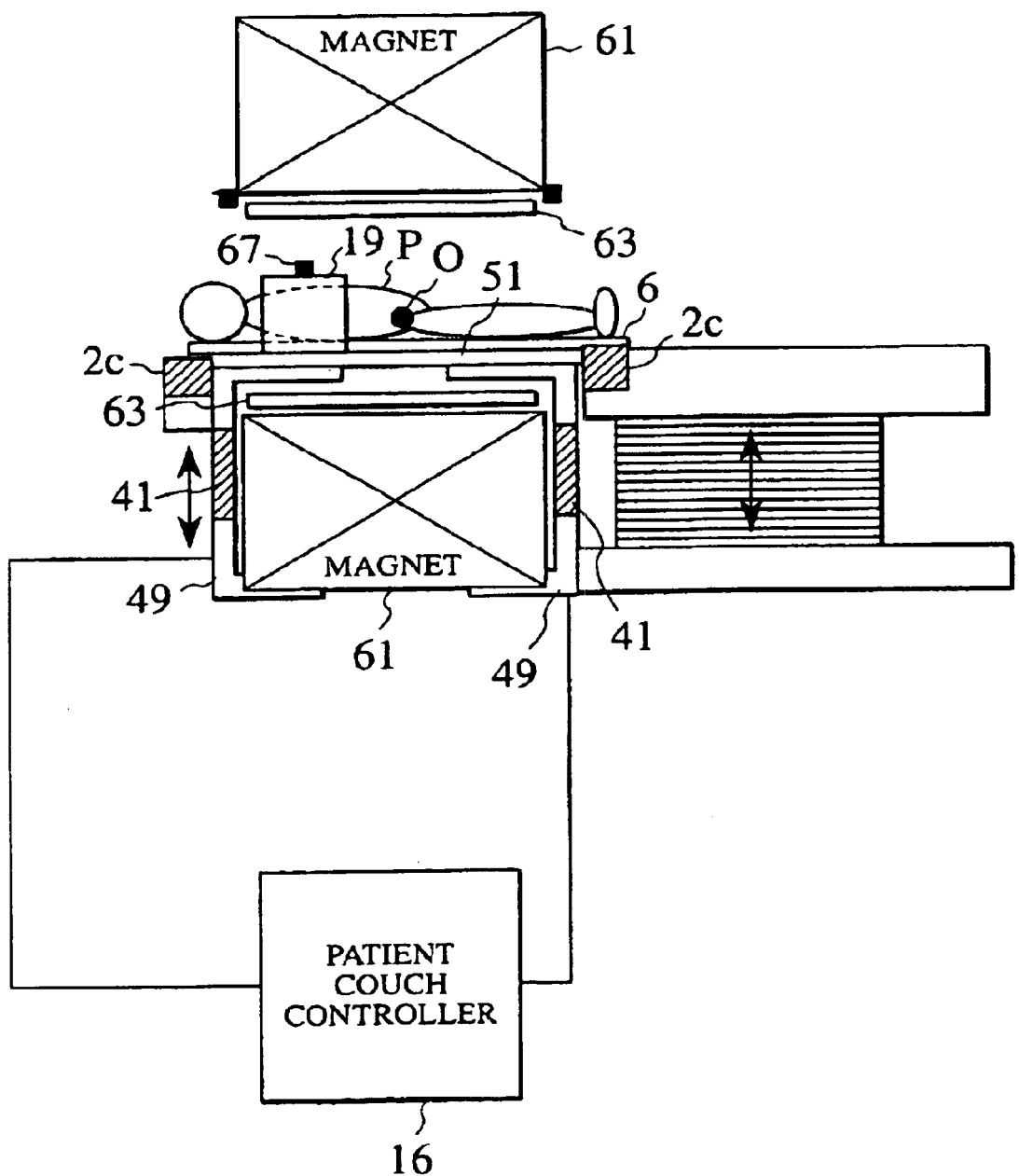
FIG. 15 is a drawing that shows a patient couch control system in a short-axis, large-diameter magnetic or vertical-field type magnet.

A variation on the above-noted embodiment is as follows. FIG. 15 shows a patient couch control system in a short-axis, large-diameter magnet or a vertical-field type magnet. The patient couch control system is a variation that is suitable for use in applying the present invention to an MRI apparatus with good open access as used in the past, of the tubular, short-axis, large-diameter magnet type.

The above-noted patient couch control system has a tubular-type short-axis, large-diameter magnet 61, a tubular-type magnetic gradient coil 63, a patient couch 63, a horizontal movement screw box 2c that has a horizontal movement mechanism, hydraulic cylinders 41 that have a vertical movement mechanism, and a patient couch controller 16. Additionally, in order to detect the position of the patient P, it is possible to provide a passive-type ball or an active-type light receiver 67 at the top pan of the T/R coil 19, and to provide an optical position sensor transmitter at the front and rear of the magnet 61. According to a patient couch control system configured in this manner, it is possible to obtain the same type of effect that is obtained by the above-described first and second embodiments.

It will be appreciated by a person skilled in the art that the present invention is not limited to the above-described embodiments, and can take be embodied as various other variations thereof.

What is claimed is:

1. A magnetic resonance imaging apparatus comprising:
   a static magnetic field generator which generates a static field;
   a gradient magnetic field generator which generates a gradient magnetic field that is superimposed on the static magnetic field;
   a main enclosure having a spherical shape, formed so as to enable enclosing of a patient, the main enclosure including the static magnetic field and the gradient magnetic field;
   a radio-frequency magnetic field pulse transmitting/receiving unit, which applies a radio-frequency pulse to a region of interest of a patient that is located within the static magnetic field, and which also receives a magnetic resonance signal that is generated from the patient;
   a patient couch, which enables movement of the patient in the main enclosure;
   a position information establishing apparatus which provides 3-dimensional position information of the region of interest of the patient; and
   a patient couch controller which moves the patient couch, based on the provided position information, so that the region of interest is re-positioned in 3-dimensions substantially either at the center of the static magnetic field, or at the center of the gradient magnetic field.

2. A magnetic resonance imaging apparatus as in claim 1, wherein the position information establishing apparatus accepts input position information based on an image of the patient that is obtained from the magnetic resonance signal.

3. A magnetic resonance imaging apparatus as in claim 1, wherein the position information establishing apparatus comprises a position detection apparatus that detects the position of the region of interest.

4. A magnetic resonance imaging apparatus as in claim 3, wherein the patient couch controller performs an initial approximate positioning of the patient couch, based on a signal from the position detection apparatus.

5. A magnetic resonance imaging apparatus as in claim 1, wherein the patient couch is capable of moving the patient in the horizontal and vertical directions.

6. A method for performing magnetic resonance imaging diagnosis in a magnetic resonance imaging apparatus having a main enclosure of spherical shape enabling enclosure of a patient, said method comprising:

placing the patient onto a patient couch that is disposed within a static magnetic field and a gradient magnetic field formed in the main enclosure;

moving the patient couch based on a signal from a position detector so that a region of interest of the patient approximately coincides with the center of the static magnetic field or the center of the gradient magnetic field;

applying a radio-frequency pulse to the region of interest of the patient, and receiving a magnetic resonance signal that is generated from the patient;

reconstructing a plurality of images of the patient, based on the magnetic resonance signal;

selecting an image that includes the region of interest from the plurality of images of the patient; and moving the patient couch, based on the selected image, so that the region of interest of the patient substantially coincides in 3-dimensions with the center of the static magnetic field or the center of the gradient magnetic field.

7. A method for performing magnetic resonance imaging diagnosis as in claim 6, wherein the step of selecting an image further comprises a step of designating the region of interest within the selected image.

8. A method for performing magnetic resonance imaging diagnosis, said method comprising:

placing a patient onto a patient couch that is disposed within a main enclosure having a spherical shape, containing a static magnetic field and a gradient magnetic field;

designating a 3-dimensional position of a region of interest of the patient; and moving the patient couch, so that the region of interest of the patient substantially coincides 3-dimensionally with the center of the static magnetic field or the center of the gradient magnetic field.

9. A method as in claim 8, wherein the step of designating a 3-dimensional position of a region of interest further comprises the steps of:

moving the patient couch so that the region of interest of the patient approximately coincides with the center of the static magnetic field or the center of the gradient magnetic field;

applying a radio-frequency pulse to the region of interest of the patient, and receiving a magnetic resonance signal that is generated from the patient;

reconstructing a plurality of images of the patient, based on the magnetic resonance signal;

selecting an image that includes the region of interest from the plurality of images of the patient; and designating the region of interest within the selected image.

10. A method as in claim 9 wherein the initial step of moving the patient couch comprises obtaining positional information from a position sensor representing a 3-dimensional position for the region of interest.

11. A method for three-dimensionally positioning a patient region of interest substantially as an optimum MR imaging position for diagnostic imaging within an MRI system including a main enclosure having a spherical shape, said method comprising:

positioning a patient region of interest at a first position within an MRI field of view;

generating MR images of the patient in three dimensions while located at said first position using a first high speed positioning scan MRI data acquisition pulse sequence;

locating and designating the patient region of interest position within said images;

generating 3-dimensional position difference data between the designated position of the patient region of interest in the images and an optimum MR imaging position;

automatically re-positioning the patient region of interest in 3-dimensions from said first, now designated, position to an optimum MR imaging position using said position difference data; and generating diagnostic MRI data, after the patient is re-positioned to said optimum MR imaging position, using a second diagnostic MRI data acquisition pulse sequence, different than said first sequence, to provide diagnostic images having improved precision and quality with reduced image distortion, non-uniformities and fat artifacts.

12. A method as in claim 11 wherein said positioning step utilizes position data provided by a position sensor that automatically senses a relative spatial position between a movable patient and a fixed MRI system.

* * * * *